(12) United States Patent
Sugimoto et al.

(10) Patent No.: US 7,998,715 B2
(45) Date of Patent: *Aug. 16, 2011

(54) METHOD OF PRODUCING LIQUID KOJI HAVING ENHANCED PLANT FIBER DEGENERATION ENZYME, LIQUID KOJI OBTAINED BY THE METHOD AND USE THEREOF

(75) Inventors: Toshikazu Sugimoto, Moriya (JP); Hiroshi Shoji, Moriya (JP)

(73) Assignee: Asahi Breweries, Ltd., Tokyo (JP)

( * ) Notice: Subject to any disclaimer, the term of this patent is extended or adjusted under 35 U.S.C. 154(b) by 471 days.

This patent is subject to a terminal disclaimer.

(21) Appl. No.: 12/067,423

(22) PCT Filed: Sep. 5, 2006

(86) PCT No.: PCT/JP2006/317504
§ 371 (c)(1),
(2), (4) Date: Mar. 19, 2008

(87) PCT Pub. No.: WO2007/034670
PCT Pub. Date: Mar. 29, 2007

(65) Prior Publication Data
US 2009/0022848 A1 Jan. 22, 2009

(30) Foreign Application Priority Data

Sep. 20, 2005 (JP) ................................. 2005-271305
Sep. 27, 2005 (JP) ................................. 2005-279905
Oct. 4, 2005 (JP) ................................. 2005-290846

(51) Int. Cl.
- C12P 1/02 (2006.01)
- C12N 1/14 (2006.01)
- C12N 9/14 (2006.01)
- C12N 9/30 (2006.01)
- C12N 9/34 (2006.01)

(52) U.S. Cl. ........ 435/171; 435/195; 435/203; 435/205; 435/254.1

(58) Field of Classification Search ........................ None
See application file for complete search history.

(56) References Cited

U.S. PATENT DOCUMENTS
6,667,066 B2 * 12/2003 Labeille et al. ................. 426/31

FOREIGN PATENT DOCUMENTS

| JP | 7-177884 A | 7/1995 |
|---|---|---|
| JP | 8-23955 A | 1/1996 |
| JP | 10-204494 A | 8/1998 |
| JP | 2003-47455 A | 2/2003 |
| JP | 2004-242532 A | 9/2004 |
| JP | 2005-318886 A | 11/2005 |
| WO | 96/11264 A1 | 4/1996 |

OTHER PUBLICATIONS

Nomachi et al. Journal of Bioscience and Bioengineering. 2002, vol. 93, No. 4, pp. 382-387.*

Koba et al. J. Ferment. Technol. 1986, vol. 64, No. 2, pp. 175-178.*
D.V. Gokhale, et al.; "Optimization of Cellulase Production by Aspergillus niger NCIM 1207"; Appl. Biochem. Biotechnol., 1991, vol. 30, No. 1, pp. 99-109.
Hitoshi Wadaka, et al.; "Preparation of Submerged Mold Culture Fluid for Rice Vinegar Mash"; Hiroshima-ken Shokuhin Kogyo Shikenjo Kenkyu Hokoku, 1980, vol. 15, pp. 13-19.
Toshikazu Sugimoto, et al.; "Enzyme Production of Aspergillus Kawachii in Submerged Cultivation Using Original Barley"; The Society for Biotechnology Taikai Koen Yoshishu, Aug. 3, 2006, vol. 58, p. 69.
Hiroshi Shoji, et al.; "Analysis of the Factor That Affect the Productivity of the Enzyme Contained in the Submerged Culture of Apergillus Kawachii Using Whole Barley"; The Society for Biotechnology Taikai Koen Yoshishu; Aug. 3, 2006, vol. 58, p. 68.
Kimio Iwano et al.; "Influence of the variety of rice and polishing rate on Japanese sake Koji making"; J. Brew. Soc. Japan, 2004, vol. 99, No. 1, pp. 55-63.
Ryozo Tonoike; Dictionary of Liquor; Tokyodo Syuppan K.K., 1980, pp. 78-79. Rikke Morkeberg, et al.; "Induction and repression of α-amylase production in batch and continuous cultures of Aspergillus oryzae"; Microbiology, 1995, vol. 141, Part 10, pp. 2449-2454.
Takeshi Akao, et al.; "Honkaku-shochu Production Using Shaking Cultured Medium of Aspergillus Kawachii"; J. Brew. Soc. Japan., 1994, vol. 89, No. 11, pp. 913-914.
Shigetoshi Sudo; "Characteristics of Acid-Stable Alpha Amylase Production by Aspergillus Kawachii", J. Brew. Soc. Japan, 1994, vol. 89, No. 10, pp. 768-774.
Hisashi Fukuda, et al.; "Improvement of Material Utilization in Sake Moromi Brewing by Addition of Cell Wall Macerating Enzymes", J. Brew. Soc. Japan, 2002, vol. 97, No. 12, pp. 808-813.
Hiroshi Shoji, et al.; "Simultaneous Production of Glucoamylase and Acid-Stable α-Amylase Using Novel Submerged Culture of *Aspergillus kawachii* NBRC4308"; Journal of Bioscience and Bioengineering; vol. 103; No. 2; Feb. 1, 2007; pp. 203-205; XP005939375.

* cited by examiner

*Primary Examiner* — Vera Afremova
(74) *Attorney, Agent, or Firm* — Sughrue Mion, PLLC

(57) ABSTRACT

An object of the present invention is to provide a method of producing liquid koji having enhanced activity of a plant fiber degradation enzyme using liquid medium without using an expensive plant fiber degradation enzyme preparation and a recombinant bacterium and methods of producing liquid koji dry product and industrial alcohol (ethanol) using the liquid koji. According to the present invention, there is provided a method of producing liquid koji having enhanced activity of a plant fiber degradation enzyme by culturing koji molds with at least one liquid medium selected from the group consisting of a liquid medium containing as culture raw material the cereal of which surface is entirely or partly covered with at least husks, a liquid medium containing as culture raw material the bean and/or the tuber of which surface is covered with hulls, and a liquid medium containing as culture raw material the amaranthus and/or the quinoa without pre-treatment such as grinding or crushing, wherein amount of the culture raw material to be used in the liquid medium is controlled to generate and accumulate simultaneously at least glucoamylase, acid-stable α-amylase and a plant fiber degradation enzyme in the koji mold culture product. There are also provided a method of producing a dry product of liquid koji with liquid medium, characterized by drying the liquid koji obtained by the above-mentioned method, and a method of producing ethanol by a fermentation method using the liquid koji.

6 Claims, 2 Drawing Sheets

METHOD OF PRODUCING LIQUID KOJI HAVING ENHANCED PLANT FIBER DEGENERATION ENZYME, LIQUID KOJI OBTAINED BY THE METHOD AND USE THEREOF

TECHNICAL FIELD

The present invention relates to a method of producing liquid koji having enhanced activities of plant fiber degradation enzymes such as cellulolytic enzymes and xylanolytic enzymes, and liquid koji obtained by the method, and a use thereof.

BACKGROUND ART

As for koji used in production of alcoholic beverages, there are solid koji, which is cultured such that spores of filamentous fungi are inoculated to raw material which has been treated with cooking and the like, and liquid koji, which is cultured such that liquid medium is prepared by adding raw material and other nutrient sources to water, and then spores of koji molds or pre-cultured mycelia of koji molds and the like are inoculate thereto.

In the conventional production of fermented foods and drinks such as alcoholic beverages including, for example, sake, shochu, soy sauce, fermented soybean paste, sweet sake and the like, what is called solid koji which is prepared with the solid culture method has been widely used. The solid culture method is the culture method in which spores of koji molds such as *Aspergillus kawachii, Aspergillus awamori, Aspergillus niger, Aspergillus oryzae, Aspergillus sojae* and the like are dispersed on solid raw material such as steam-cooked cereals to allow koji molds to grow on the solid surface.

For instance, for the production of shochu, the solid koji such as *Aspergillus kawachii* and *Aspergillus awamori* have been widely used. However, as the solid culture method is a culture system in which raw materials and koji molds disperse unevenly, it is difficult to make even the factors such as temperature, water content, and various nutrient compositions, and the solid culture method is very complicated in culture control. In addition, the production of koji is often conducted under open conditions, and cares are required in terms of quality control so as to prevent contamination with other bacteria. Therefore, the solid culture method is unsuitable for large-scale production.

In contrast, the liquid culture method is easy to culture control and quality control, so it is suitable for efficient production. However, due to the reason that, for example, enzymatic activity is insufficient for brewing shochu, the culture product obtained by liquid culturing koji molds is rarely used as shochu koji.

In addition to the above-mentioned reasons, a major reason of the culture product obtained with the liquid culture method not being used for producing fermented foods and drinks such as shochu is that the behavior of koji molds to produce enzymes such as amylase and cellulase in the liquid culture is known to be much different from that in the solid culture, and productivity thereof is also known to be poor overall (see Non-Patent Documents 1 and 2).

In production of the alcoholic beverages such as shochu, alcohol is usually generated by simultaneous saccharification and fermentation. Therefore, saccharolytic enzymes from koji molds, which affect supplying glucose to the koji molds, particularly glucoamylase and acid-stable α-amylase are key enzymes in the alcoholic fermentation. However, it is known that activity of glucoamylase is remarkably low in the culture product obtained with the liquid culture method and production behavior thereof is also much different from that in the solid culture (see Non-Patent Documents 3 to 6).

As a method of improving glucoamylase activity of koji molds, there are reported the method of culturing koji molds while giving stresses on the growth of mycelia (see Patent Document 1) and the method of adding roasted cereals to koji mold culture fluid (see Patent Document 2). The method disclosed in Patent Document 1 conducts culture on porous membrane or in inclusive immobilization agent having air gaps to allow expression of the novel gene glaB that encodes glucoamylase, to thereby enhance enzymatic activity. Accordingly, the method requires strict control or specific culture devices, and thus it is not practical. The method disclosed in Patent Document 2 cultures koji molds in liquid medium using roasted cereals as, at least, a portion of the raw material, which requires an additional production step of roasting cereals.

The inventors of the present invention provided an invention related to a method of culturing koji molds using liquid medium containing the saccharides which the koji molds hardly decompose (see Patent Document 3). By liquid culturing koji molds with the invention, a koji mold culture product having high activity of glycolytic enzymes such as glucoamylase, which can be used for producing fermented foods and drinks such as sake, can be obtained conveniently and inexpensively.

On the other hand, recently, the molecular biological analysis on acid-stable α-amylase has been conducted to the details (see Non-Patent Document 7). The analysis has reported as follows: A white koji mold has two different amylase genes which are respectively responsible for two different characteristics, that is, acid-unstable α-amylase and acid-stable α-amylase. The expression behaviors of the respective genes are much different from each other. In liquid culturing, the acid-unstable α-amylase is sufficiently produced, while the acid-stable α-amylase, a key enzyme for brewing shochu is hardly produced.

For producing shochu, brewing is conducted under low-pH environments for preventing the shochu mash from putrefaction. The acid-unstable α-amylase contributes very little to glycolysis in shochu brewing because it is deactivated precisely under low-pH conditions. Therefore, it is indispensable for producing shochu that the acid-stable α-amylase is produced with high yield, which is thought to contribute to the glycolysis in shochu brewing, by liquid culturing koji molds.

The production behavior of acid stable α-amylase in liquid culturing koji molds has been investigated in detail and reported. However, the method uses synthetic medium containing peptone and citrate buffer solution, and requires an culture time of 100 hours or more, so it would be difficult to apply to actual shochu brewing (see Non-Patent Documents 8 to 10).

The inventors of the present invention have already developed a method of producing liquid koji sufficiently having enzymatic activities of glucoamylase and acid-stable α-amylase which are necessary for producing shochu, which involves culturing white koji molds and/or black koji molds in liquid medium containing the cereal of which surface is covered with husks as culture raw material to generate and accumulate simultaneously glucoamylase and acid-stable α-amylase in the culture product. The inventors have succeeded in producing shochu using the liquid koji for the first time (see, for example, the specification of Japanese Patent Application No. 2004-350661).

Meanwhile, there has been conducted investigation on plant fiber degradation enzymes produced with koji in order to additionally improve productivity of sake and shochu. It has been reported that utilization ratio of the raw material of sake mash is improved when plant fiber degradation enzymes such as a cellulolytic enzyme, a xylanolytic enzyme, and a pectolytic enzyme are employed in production of sake (see, Non-patent Documents 11 and 12).

It has been also reported that alcohol yield in shochu is improved by creating the recombinant shochu koji molds to which the cellulolytic enzyme gene of *Trichoderma viride* is introduced and producing shochu with the recombinant shochu koji molds (see Non-patent Document 13).

As described above, it is widely known that improvement in productivity of the plant fiber degradation enzymes to be used in production of sake or shochu is extremely important for promoting efficiency in production of fermented foods and drinks such as sake or shochu.

However, employing the expensive plant fiber degradation enzyme preparation in production of sake may increase cost, and is not preferable.

In addition, using the recombinant shochu koji mold would let the consumer worries about safety, and is not also preferable.

By the way, ethanol as industrial alcohol is used as raw material for producing foods and drinks such as sweet sake, vinegar and the like, or as raw material for producing industrial chemicals such as flavor, detergent and the like. Further, the ethanol is expected recently to serve as novel energy source which is alternative to a fossil fuel such as petroleum. For instance, investigations and developments of an alcohol fuel such as E3 gasoline which is obtained by mixing gasoline with 3% of ethanol are promoted.

When the industrial alcohol is produced by fermentation method using cereals or tubers as raw material, an enzyme preparation (liquefying enzymes or saccharolytic enzymes) needs to be used for high enzymatic activities (see, for example, Non-patent Document 14).

However, use of the enzyme preparation causes a problem that, in addition to high cost, mashing can not be conducted at high concentration. The mash produced with an enzyme preparation generally has an alcohol content of about 8%. Thus, mashing at higher concentration has been expected for improving productivity.

There may be suggested to use solid koji in which koji molds are grown on the surface of cereals or beans, instead of the enzyme preparation. However, the solid koji is not suitable for large-scale production because it has to be produced in a specific culture mode, that is, solid culture.

On the other hand, liquid koji in which koji molds are cultured in liquid medium is able to control culture easily, so that it is suitable for efficient production.

However, it is known to persons skilled in the art that liquid koji does not provide enzymatic activities required for the alcohol fermentation sufficiently, so there has been no examples where liquid koji is used in actual production.

Non-patent Document 1: Iwashita K. et al: Biosci. Biotechnol. Biochem., 62, 1938-1946 (1998)
Non-patent Document 2: Yuichi Yamane et al.: Journal of the Brewing Society of Japan, 99, 84-92 (2004)
Non-patent Document 3: Hata Y. et al.: J. Ferment. Bioeng., 84, 532-537 (1997)
Non-patent Document 4: Hata Y. et al.: Gene., 207, 127-134 (1998)
Non-patent Document 5: Ishida H. et al.: J. Ferment. Bioeng., 86, 301-307 (1998)
Non-patent Document 6: Ishida H. et al.: Curr. Genet., 37, 373-379 (2000)
Non-patent Document 7: Nagamine K. et al.: Biosci. Biotechnol. Biochem., 67, 2194-2202 (2003)
Non-patent Document 8: Sudo S. et al.: J. Ferment. Bioeng., 76, 105-110 (1993)
Non-patent Document 9: Sudo S. et al.: J. Ferment. Bioeng., 77, 483-489 (1994)
Non-patent Document 10: Shigetoshi Sudo et al.: Journal of the Brewing Society of Japan, 89, 768-774 (1994)
Non-patent Document 11: Yoshizawa et al. Journal of the Brewing Society of Japan, 76, 284-286 (1981)
Non-patent Document 12: Fukuda et al. Journal of Bioscience and Bioengineering, 79, 299-302 (2001)
Non-patent Document 13: Nomachi W. et al., J. Biosci. Bioeng., 93(4), p 382-387, 2002
Non-patent Document 14: Encyclopedia of Brewing, p 352-371, Asakura Publishing, Co., Ltd., first edition issued on Nov. 10, 1988
Patent Document 1: JP 11-225746 A
Patent Document 2: JP 2001-321154 A
Patent Document 3: JP 2003-265165 A

DISCLOSURE OF THE INVENTION

Problems to be Solved by the Invention

The inventors of the present invention have made extensive studies to solve the conventional problems as described above.

As a result, the inventors of the present invention have found that, in the method, which the inventors of the present invention has been developed, of producing liquid koji having high activities of glucoamylase and acid-stable α-amylase (see, for example, a specification of Japanese Patent Document No. 2004-350661), in which white koji molds and/or black koji molds are cultured in a liquid medium containing the cereal of which surface is covered with husks as culture raw material to generate and accumulate simultaneously glucoamylase and acid-stable α-amylase in the culture product, activity of plant fiber degradation enzymes can be enhanced by controlling amount of the culture raw material to be used in the liquid medium. According to the finding, the present invention has been completed.

It should be noted that there has not been known production behavior nor production method in high yields, of plant fiber degradation enzyme, in producing liquid koji with the raw material having husks as disclosed in the specification of Japanese Patent Application No. 2004-350661. Further, there has not been reported production of shochu using the liquid koji at all.

It is an object of the first aspect of the present invention to provide a method of producing liquid koji having enhanced activity of plant fiber degradation enzymes, by liquid culturing instead of solid culturing without using an expensive plant fiber degradation enzyme preparation nor a recombinant bacterium.

Further, it is another object of the first aspect of the present invention to provide a method of efficiently producing fermented foods and drinks such as shochu, by using the liquid koji having enhanced activity of plant fiber degradation enzymes.

The liquid koji is in liquid state, so it provides a merit that handling thereof such as pumping is easy. However, a dry product obtained by treating the liquid koji with a method such as vacuum drying is supposed to contribute to efficiency in producing fermented foods and drinks such as shochu, if only the similar fermentation property to that of the liquid koji can be attained.

It is an object of the sixth aspect of the present invention to provide a method of producing a liquid koji dry product which can contribute to efficiency in producing fermented foods and drinks such as shochu.

That is, the object of the sixth aspect of the present invention is to provide a method of producing a liquid koji dry product which has high activities of glucoamylase, acid-stable α-amylase, and plant fiber degradation enzymes and is further excellent in handling property.

Further, the object of the sixth aspect of the present invention is to provide a method of efficiently producing fermented foods and drinks such as shochu, by using the liquid koji dry product as described above.

It is an object of the 21st aspect of the present invention to develop liquid koji sufficiently having enzymatic activity required for alcohol fermentation, and to establish a method of efficiently producing industrial alcohol (ethanol) by fermentation method using the liquid koji.

Liquid koji to be used for producing industrial alcohol (ethanol) needs to have high activity of glycolytic enzymes such as glucoamylase and acid-stable α-amylase, and of plant fiber degradation enzymes. However, there has not yet been disclosed a technique by which liquid koji having high enzymatic activity is obtained by culturing koji molds in liquid medium. In other words, the acid-stable α-amylase is generally stated as an enzyme which is not generated by liquid culturing, so liquid koji having high acid-stable α-amylase activity has not yet been developed.

Thus, as described above, an object of the 21st aspect of the present invention is to develop liquid koji having high activities of glucoamylase, acid-stable α-amylase and plant fiber degradation enzymes, and to establish a method of efficiently producing industrial alcohol (ethanol) by fermentation method using the liquid koji.

Means for Solving the Problems

According to a first aspect of the present invention, there is provided a method of producing liquid koji having enhanced activity of a plant fiber degradation enzyme by culturing koji molds with at least one liquid medium selected from the group consisting of a liquid medium containing as culture raw material the cereal of which surface is entirely or partly covered with at least husks, a liquid medium containing as culture raw material the bean and/or the tuber of which surface is covered with hulls and a liquid medium containing as culture raw material the amaranthus and/or the quinoa without pre-treatment such as grinding or crushing, in which amount of the culture raw material to be used in the liquid medium is controlled to generate and accumulate simultaneously at least glucoamylase, acid-stable α-amylase and a plant fiber degradation enzyme in the koji mold culture product.

According to a second aspect of the present invention, there is provided the method of producing liquid koji according to the first aspect of the invention, in which the plant fiber degradation enzyme comprises a cellulolytice enzyme and/or a xylanolytic enzyme.

According to a third aspect of the present invention, there is provided the method of producing liquid koji according to the first aspect of the invention, in which the koji molds comprise white koji molds and/or black koji molds.

According to a fourth aspect of the present invention, there is provided the method of producing liquid koji according to the first aspect of the invention by culturing koji molds with at least one liquid medium selected from the group consisting of a liquid medium containing as culture raw material the cereal of which surface is entirely or partly covered with at least husks, a liquid medium containing as culture raw material the bean and/or the tuber of which surface is covered with hulls and a liquid medium containing as culture raw material the amaranthus and/or the quinoa without pre-treatment such as grinding or crushing, in which amount of the culture raw material to be used in the liquid medium is controlled to 1.4 to 1.8% (w/vol), and the culture condition is made at 37° C. for 42 hours to generate and accumulate simultaneously at least glucoamylase, acid-stable α-amylase and a plant fiber degradation enzyme in the koji mold culture product.

According to a fifth aspect of the present invention, there is provided liquid koji, which is obtained by the method according to any one of the first to fourth aspects.

According to a sixth aspect of the present invention, there is provided a method of producing a dry product of liquid koji with liquid medium comprising, drying the liquid koji according to the fifth aspect of the invention.

According to a seventh aspect of the present invention, there is provided a liquid koji dry product, which is obtained by the method according to the sixth aspect of the invention.

According to an eighth aspect of the present invention, there is provided a method of producing an enzyme preparation comprising, using the liquid koji according to the fifth aspect of the invention.

According to a ninth aspect of the present invention, there is provided an enzyme preparation, which is obtained by the method according to the eighth aspect of the invention.

According to a tenth aspect of the present invention, there is provided a method of producing enzymes by culturing koji molds with at least one liquid medium selected from the group consisting of a liquid medium containing as culture raw material the cereal of which surface is entirely or partly covered with at least husks, a liquid medium containing as culture raw material the bean and/or the tuber of which surface is covered with hulls and a liquid medium containing as culture raw material the amaranthus and/or the quinoa without pre-treatment such as grinding or crushing, in which amount of the culture raw material to be used in the liquid medium is controlled to generate and accumulate simultaneously at least glucoamylase, acid-stable α-amylase and a plant fiber degradation enzyme in the koji mold culture product.

According to an eleventh aspect of the present invention, there is provided the method of producing enzymes according to the tenth aspect of the invention, in which the plant fiber degradation enzyme comprises a cellulolytice enzyme and/or a xylanolytic enzyme.

According to a twelfth aspect of the present invention, there is provided the method of producing enzymes according to the tenth aspect of the invention, in which the koji molds comprise white koji molds and/or black koji molds.

According to a thirteenth aspect of the present invention, there is provided the method of producing enzymes according to the tenth aspect of the invention by culturing koji molds with at least one liquid medium selected from the group consisting of a liquid medium containing as culture raw material the cereal of which surface is entirely or partly covered with at least husks, a liquid medium containing as culture raw material the bean and/or the tuber of which surface is covered with hulls and a liquid medium containing as culture raw material the amaranthus and/or the quinoa without pre-treatment such as grinding or crushing, in which amount of the culture raw material to be used in the liquid medium is controlled to 1.4 to 1.8% (w/vol), and the culture condition is made at 37° C. for 42 hours to generate and accumulate simultaneously at least glucoamylase, acid-stable α-amylase and a plant fiber degradation enzyme in the koji mold culture product.

According to a fourteenth aspect of the present invention, there is provided an enzyme, obtained by the method according to any one of the tenth to thirteenth aspects of the invention.

According to a fifteenth aspect of the present invention, there is provided a method of producing a fermented food or drink comprising, using the liquid koji according to the fifth aspect of the invention.

According to a sixteenth aspect of the present invention, there is provided a method of producing a fermented food or drink according to the fifteenth aspect of the invention, in which the fermented food or drink is shochu.

According to a seventeenth aspect of the present invention, there is provided a method of producing a fermented food or drink comprising, using the liquid koji dry product according to the seventh aspect of the invention.

According to an eighteenth aspect of the present invention, there is provided a method of producing a fermented food or drink comprising, using the enzyme preparation according to the ninth aspect of the invention.

According to a nineteenth aspect of the present invention, there is provided a method of producing a fermented food or drink comprising, using the enzyme according to the fourteenth aspect of the invention.

According to a twentieth aspect of the present invention, there is provided a fermented food or drink, which is obtained by the method according to any one of the fifteenth to nineteenth aspects of the invention.

According to a 21st aspect of the present invention, there is provided a method of producing ethanol comprising, using the liquid koji according to the fifth aspect of the invention.

According to a 22nd aspect of the present invention, there is provided a method of producing ethanol comprising, using the liquid koji dry product according to the seventh aspect of the invention.

According to a 23rd aspect of the present invention, there is provided a method of producing ethanol comprising, using the enzyme preparation according to the ninth aspect of the invention.

According to a 24th aspect of the present invention, there is provided a method of producing ethanol comprising, using the enzyme according to the fourteenth aspect of the invention.

According to a 25th aspect of the present invention, there is provided ethanol, obtained by the method according to any one of the 21st to 24th aspects of the invention.

Effect of the Invention

According to the first aspect of the present invention, there can be produced liquid koji having enhanced activity of plant fiber degradation enzymes such as a cellulolytic enzyme (cellulase) and a xylanolytic enzyme, by liquid culturing instead of solid culturing without using an expensive plant fiber degradation enzyme preparation nor a recombinant bacterium.

Further, according to the first aspect of the present invention, there is provided a method of efficiently producing fermented foods and drinks such as shochu, by using the liquid koji having enhanced activity of plant fiber degradation enzymes.

According to the first aspect of the present invention, for example, in the case where shochu is produced as the fermented foods and drinks, viscosity of shochu mash can be expected to be decreased to thereby significantly improve workability. In addition, it also can be expected improvement in utilization ratio of the raw material such as increase in an alcohol yield, leading to additional efficiency in producing fermented foods and drinks such as shochu.

According to the sixth aspect of the present invention, there can be produced liquid koji dry product which has high activities of glucoamylase, acid-stable α-amylase and plant fiber degradation enzymes, and is further excellent in handling property.

The product is in dry state, so there is a merit that it is timely available even for unexpected production.

Further, owing to the properties, the liquid koji dry product can be used for efficiently producing various fermented foods and drinks.

For instance, by using the liquid koji dry product produced according to the sixth aspect of the present invention, the fermentation degree nearly equal to that of shochu mashes obtained by using undried liquid koji or conventional solid koji, can be obtained, and the produced shochu has quality nearly equal to that of the shochu produced by using the undried liquid koji or the solid koji without organoleptic inferiority.

Further, according to the 21st aspect of the present invention, there is provided a method of producing ethanol by a fermentation method using the liquid koji.

According to the method, it becomes possible to produce mash having alcohol content nearly as high as that of ethanol which is obtained with a method of producing ethanol by fermentation using the conventional solid koji. The production of mash having high alcohol content can contribute to scale reduction and energy saving.

According to the 21st aspect of the present invention, industrial alcohol (ethanol) can efficiently be produced by fermentation method using the liquid koji sufficiently having enzymatic activity required for alcohol fermentation.

BEST EMBODIMENT FOR CARRYING OUT THE INVENTION

Figure 1:
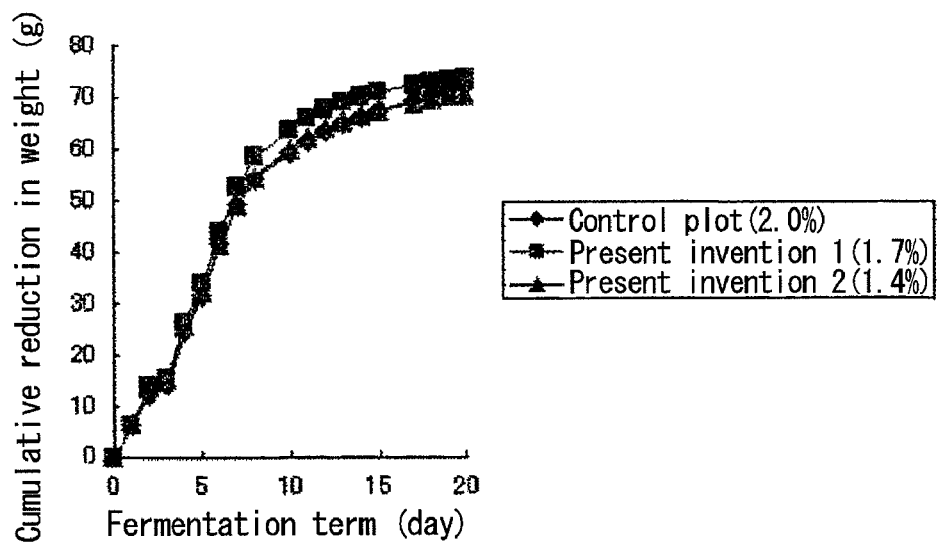
FIG. 1 is a graph showing the processes of fermentation in production of barley shochu using various liquid koji having different amounts of crude barley to be used in Example 2.

Hereinafter, the present invention will be described in detail.

A first aspect of the present invention relates to a method of producing liquid koji having enhanced activity of a plant fiber degradation enzyme by culturing koji molds with at least one liquid medium selected from the group consisting of a liquid medium containing as culture raw material the cereal of which surface is entirely or partly covered with at least husks, a liquid medium containing as culture raw material the bean and/or the tuber of which surface is covered with hulls and a liquid medium containing as culture raw material the amaranthus and/or the quinoa without pre-treatment such as grinding or crushing, wherein amount of the culture raw material to be used in the liquid medium is controlled to generate and accumulate simultaneously at least glucoamylase, acid-stable α-amylase and a plant fiber degradation enzyme in the koji mold culture product.

In the first aspect of the present invention, there is used at least one liquid medium selected from the group consisting of a liquid medium containing as culture raw material the cereal of which surface is entirely or partly covered with at least husks, a liquid medium containing as culture raw material the bean and/or the tuber of which surface is covered with hulls and a liquid medium containing as culture raw material the amaranthus and/or the quinoa without pre-treatment such as grinding or crushing, and koji molds are cultured in the liquid medium. Therefore, it takes much time for saccharification of starches in the cereals, the rate of releasing saccharides into culture system is suppressed, and enzymatic activity of liquid koji is enhanced.

In the first aspect of the present invention, examples of the cereal to be used as culture raw material of liquid koji comprise barley, naked barley, rice, wheat, buckwheat, barnyard millet, foxtail millet, millet, kaoliang, corn and the like. The raw materials need to have the form of which surface is entirely or partly covered with at least husks. There can be used an unpolished stuff or that having equal to or more of the polishing ratio at which it has been polished so that husks are at least remained on the surface of kernels, and crude rice, crude barley, and the like also can be used. In the case of rice, crude rice, rice with all chaffs and rice with a part of chaffs may be used.

When the cereal is barley, there can be used the unpolished stuff having a polishing ratio of 100%, or provided that the polishing ratio of the unpolished stuff is defined as 100%, the stuff having a polishing ratio not less than the value determined by subtracting the husk ratio of barley (generally 7 to 8%) from the polishing ratio of the unpolished stuff (100%), i.e., about 92% to 93%.

Here, the term "polishing ratio" refers to the remained ratio of cereals after the cereals are polished. For instance, the term "polishing ratio of 90%" means that 10% of the husks or the like on the surface layer portion of cereals is shaved away. In the present invention, the term "crude barley" comprises those from unpolished barley to polished barley having husks remained on kernels' surface, that is, the stuff having polishing ratio of 90% or more. In addition, the term "husk" refers to the outside part that covers the surface of a cereal particle.

In the first aspect of the present invention, examples of the bean and the tuber used as culture raw material for the liquid koji comprise soybean, red bean, sweet potato and the like. Those culture raw materials are only subjected that the soil on their hulls washed away, but are not subjected to processes such as cutting, crushing and the like.

In the first aspect of the present invention, "amaranthus" to be used as culture raw material for the liquid koji is a generic term of plants belonging to the genus Amaranthus of the family Amaranthaceae. Among cereals, amaranthus has high protein content and the content of lysine, which is one of amino acids, is nearly equal to that in soybean. Besides, amaranthus is a highly nutritious cereal containing large amounts of calcium, iron, and fibers when compared to polished rice. The countries of origin are specific areas of South/Central American countries, India, Himalayas, and Nepal. On the other hand, quinoa is an annual herb of Agatha family, which is mainly cultivated in highlands such as the Andes located in the southern part of Peru and the western part of Bolivia. Quinoa is rich in minerals, vitamins, proteins, and dietary fibers.

Amaranthus and quinoa to be used as culture raw materials may be used alone or in combination. Those raw materials may be directly used for preparing liquid medium without being subjected to pre-treatments such as grinding or crushing.

The above-mentioned culture raw materials are used alone, or two or more of them are used in combination for preparing the following liquid medium.

That is, the culture raw materials are mixed with water to prepare a liquid medium.

In the present invention, it is necessary to control amount of the culture raw material to be used in the liquid medium.

In general, plant fiber degradation enzymes such as a cellulolytic enzyme (cellulase) and a xylanolytic enzyme (xylanase) are enhanced when amount of the culture raw material is slightly fewer than that preferable for that glucoamylase and acid-stable α-amylase are generated and accumulated in a balanced manner.

The amount of the culture raw material to be used in the liquid medium is within a range in which glucoamylase and acid-stable α-amylase are selectively generated and accumulated during the koji molds are cultured and, at the same time, the plant fiber degradation enzymes such as the cellulolytic enzyme (cellulase) and the xylanolytic enzyme are enhanced.

To be specific, for instance, when barley or naked barley is used as culture raw material, liquid medium is prepared by adding 1 to 20% (w/vol) of the barley or naked barley to water. When unpolished barley or naked barley is used, more preferably, liquid medium is prepared with the addition of 8 to 10% (w/vol). When 95%-polished barley or naked barley is used as culture raw material, more preferably, liquid medium is prepared with the addition of 1 to 4% (w/vol).

As described in the fourth aspect of the present invention, when the culture condition is at 37° C. for 42 hours, liquid medium is prepared by adding 1.4 to 1.8% (w/vol) or preferably 1.4 to 1.7% (w/vol) of the barley or naked barley to water. The same is applied to the case where unpolished barley or naked barley is used and the case where 95%-polished barley or naked barley is used as raw material.

When crude rice from which chaffs are removed is used as culture raw material, liquid medium is prepared by adding 1 to 20% (w/vol), preferably 5 to 13% (w/vol), or more preferably 8 to 10% (w/vol) of crude rice to water.

When bean is used as culture raw material, liquid medium is prepared by adding 1 to 10% (w/vol) of bean to water, or preferably, by adding 8 to 10% (w/vol) of soybean or 1 to 2% (w/vol) of red bean to water. When tuber is used as culture raw material, liquid medium is prepared by adding 1 to 10% (w/vol) of tuber to water.

When amaranthus is used as culture raw material, liquid medium is prepared by adding 1.5 to 15% (w/vol), preferably 2 to 10% (w/vol), or more preferably 2 to 8% (w/vol) of amaranthus to water. When quinoa is used as culture raw material, liquid medium is prepared by adding 1.5 to 7% (w/vol), preferably 2 to 6% (w/vol), or more preferably 2 to 4% (w/vol) of quinoa to water. The amounts of the culture raw materials to be used for the blending may appropriately be selected because the optimal amounts vary dependent on the kinds of the culture raw materials to be used, the polishing degrees of the culture raw materials, and the like.

When koji molds are cultured in the liquid medium to which the culture raw material is added in an amount within the above-mentioned range, there can be produced liquid koji which has enzymatic activity (glucoamylase activity and acid-stable α-amylase activity) sufficient to be used for producing fermented foods and drinks such as shochu and, at the same time, has enhanced activity of plant fiber degradation enzymes such as a cellulolytic enzyme (cellulase) and a xylanolytic enzyme (xylanase).

When the amount of the culture raw material to be used exceeds the upper limit, the liquid koji having enhanced activity of plant fiber degradation enzymes such as a cellulolytic enzyme (cellulose) and a xylanolytic enzyme (xylanase) can not be obtained. Further, viscosity of the culture liquid increases and supply of oxygen or air required for aerobically culturing koji molds becomes insufficient. That decreases oxygen content in the culture product, restricts culture progress, and is not preferred. On the other hand, when the amount of the raw material to be used is less than the lower limit, the intended enzymes can not be produced in high yields.

Starches included in the culture raw material may be preliminarily gelatinized before culturing. Gelatinizing starches may be conducted according, but not particularly limited, to any of the conventional methods comprising a steaming method, a roasting method and the like. In the step of sterilizing liquid medium as described later, when the starches are heated to the gelation temperature or higher by sterilization at high temperatures and high pressures, gelatinization of starches is simultaneously carried out by such the treatment.

In addition to the above-mentioned culture raw material, it is preferable that an organic substance, an inorganic salt, and the like be appropriately added as nutrient source to the liquid medium.

Those additives are not particularly limited as long as they are generally used for culturing koji molds. Examples of the organic substance comprise rice bran, wheat bran, corn steep liquor, soybean cake and defatted soybean. Examples of the inorganic salt include aqueous compounds such as an ammonium salt, a nitrate salt, a potassium salt, an acid phosphate salt, a calcium salt, and a magnesium salt. Two or more organic substances and/or inorganic salts may simultaneously be used. The addition amounts thereof are not particularly limited as long as growth of the koji molds is promoted. The addition amount of the organic substance is preferably about 0.1 to 5% (w/vol) and the amount of the inorganic salt is preferably about 0.1 to 1% (w/vol).

The liquid medium of koji molds thus obtained may be subjected to sterilization treatment if necessary and the treatment procedures are not particularly limited. For example, it may be the high-temperature and high-pressure sterilization method carried out at a temperature of 121° C. for 15 minutes.

The sterilized liquid medium is cooled down to a culture temperature, and then koji molds are inoculated to the liquid medium.

The koji molds to be used in the first aspect of the present invention is the koji molds capable of producing a glycolytic enzyme, preferably one capable of producing glucoamylase and acid-stable α-amylase. Examples thereof comprise white koji molds such as *Aspergillus kawachii*, black koji molds such as *Aspergillus awamori* and *Aspergillus niger*, and yellow koji molds such as *Aspergillus oryzae* and *Aspergillus sojae*.

The white koji molds, the black koji molds, and the yellow koji molds may be used alone, or two or more of them may be used in combination. It is preferable that the white koji molds and the black koji molds be used alone, or both of them be used in combination.

Those koji molds may be used for the single strain culture or for the mixed culture with two or more homologous or heterogeneous strains. It is allowed to use either form of the spores or the mycelia obtained in pre-culture. However, the mycelia is preferably used because shorter times are required for the logarithmic growth phase. The amount of the koji molds to be inoculated into the liquid medium is not particularly limited, but the number of the spores may be in the range of about $1\times10^4$ to $1\times10^6$ per ml of the liquid medium. For the mycelia, about 0.1 to 10% of the pre-culture liquid is preferably inoculated.

The culture temperature of the koji molds is preferably 25 to 45° C., or more preferably 30 to 40° C., but not particularly limited as long as the growth is not adversary affected. If the culture temperature is low, it tends to be contaminated by infectious microbes as growth of the koji molds becomes slow. The culture time is preferably in the range of 24 to 72 hours.

The culture apparatus may be any of those capable of carrying out liquid culture. The koji molds have to be cultured aerobically. Thus, the culture should be conducted under aerobic conditions in which oxygen or air can be supplied into the medium. In addition, it is preferable to stir the medium so that the raw materials, oxygen, and the koji molds can be uniformly distributed in the apparatus during culture. The stirring conditions and the amount of aeration may be arbitrary as long as aerobic culture environment is maintained and thus may be appropriately selected depending on the culture apparatus, the viscosity of the medium and the like.

By culturing with the above-mentioned culture method, the enzymes such as glucoamylase and acid-stable α-amylase are simultaneously generated in a balanced manner, and at the same time, activity of plant fiber degradation enzymes such as a cellulolytic enzyme (cellulase) and a xylanolytic enzyme is enhanced in the liquid koji.

The liquid koji in the present invention comprises a culture product itself, a culture liquid obtained from the culture product by centrifugal separation or the like, a concentrate or a dry product thereof, and the like.

As described above, according to the above-mentioned culture method, the enzymes such as glucoamylase, acid-stable α-amylase, a cellulolytic enzyme, and a xylanolytic enzyme are highly produced.

Therefore, the method of producing enzymes described in the tenth aspect of the present invention is substantially the same as the method of producing liquid koji described above.

The liquid koji according to the fifth aspect of the present invention can be produced by the method according to the first aspect of the present invention.

The liquid koji according to the fifth aspect of the present invention, which is obtained by the production method according to the first aspect of the present invention, can be suitably used for producing fermented foods and drinks such as shochu, sake, soy sauce, miso and sweet sake, as described in the fifteenth aspect of the present invention.

The liquid koji may be used instead of the solid koji, for instance, in the case of producing shochu as described in the sixteenth aspect of the present invention, at the stage of mashing shochu mash; in the case of producing sake, at the stages of mashing yeast or sake mash; in the case of producing soy sauce, at the stage of piling; in the case of producing miso, at the stage of mashing; in the case of producing sweet sake, at the stage of mashing.

When fermented foods and drinks are produced using the above-mentioned liquid koji, all steps may be carried out in liquid phase. A method of producing fermented foods and drinks in liquid phase through the whole steps, for instance, when shochu is produced, is that corn, wheat, rice, potato, sugar cane and the like are as raw material heated at about 80° C. to liquefy by dissolving with a heat-resistant enzyme preparation, the above liquid koji and yeast are added thereto to allow the mash to alcohol ferment, and then it is distillated under normal pressure or reduced pressure and the like.

The liquid koji obtained by the method according to the first aspect of the present invention can be utilized for an enzyme preparation, a pharmaceutical such as a digestive agent and the like because of high enzymatic activity thereof. In this case, the resultant koji mold culture product may be concentrated and purified to desired extent by conventional method, and an appropriate excipient, thickening agent, sweetener and the like are added thereto.

According to the sixth aspect of the present invention, there is provided a method of producing a liquid koji dry product comprising, drying the liquid koji which is obtained as described above.

The preferred drying method comprises freeze drying, and, in particular, vacuum freeze-drying is more preferable because inactivation of an enzyme hardly occurs. The vacuum freeze-drying may be conducted according to conventional method. Conditions for the vacuum freeze-drying are not particularly limited, but in general, pre-freezing may be conducted at a temperature of from −10 to −40° C. for 1 to 6 hours and drying may then be conducted at 5 to 30° C. for 10 to 30 hours at a degree of vacuum of 1 Torr or less, or preferably 0.7 Torr or less.

In this manner, an intended liquid koji dry product can be produced.

The liquid koji dry product according to the seventh aspect of the present invention, which is obtained by the production method according to the sixth aspect of the present invention, can suitably be used for producing fermented foods and drinks as described in the seventeenth aspect of the present invention.

The liquid koji dry product may be used instead of the solid koji or the liquid koji for instance, in the case of producing sake, at the stage of mashing yeast or sake mash; in the case of producing shochu, at the stage of mashing shochu mash; in the case of producing soy sauce, at the stage of piling; in the case of producing miso, at the stage of mashing; in the case of producing sweet sake, at the stage of mashing.

In the case where fermented foods and drinks are produced using the liquid koji dry product, there may be used liquid koji dry product an enzyme preparation without modification, the product obtained by mixing steamed barley, yeast cells and the liquid koji in advance and drying, or the preparation obtained by mixing the various dried raw materials. As described above, if the raw materials are integrated into a sort of kit, the kit would serve as a simple starter by which fermented foods and drinks such as shochu can be conducted with addition of water.

When fermented foods and drinks are produced using the above-mentioned liquid koji dry product, all steps may be carried out in liquid phase. A method of producing fermented foods and drinks in liquid phase through the whole steps, for instance, when shochu is produced, is that corn, wheat, rice, potato, sugar cane and the like are as raw material heated at about 80° C. to liquefy by dissolving with a heat-resistant enzyme preparation, the above liquid koji and yeast are added thereto to allow the mash to alcohol ferment, then it is distillated under normal pressure or reduced pressure and the like.

The liquid koji obtained by the above-mentioned production method is used for producing ethanol by a fermentation method according to the 21st aspect of the present invention. In production of ethanol, industrial alcohol (ethanol) can be produced according to a known method of producing industrial alcohol (ethanol) except that the liquid koji is used instead of solid koji.

An example of the method of producing ethanol by a fermentation method is represented hereinbelow.

The raw material to be used for producing ethanol may be starch-containing raw material, and examples thereof comprise cereals such as barley, naked barley, rice, wheat, buckwheat, barnyard millet, foxtail millet, millet, kaoliang and corn; and tubers such as sweet potato and cassava.

The production of ethanol by fermentation method can be conducted using a continuous steaming and boiling apparatus such as a low-temperature continuous steaming and boiling apparatus. First, yeast capable of producing ethanol such as shochu yeast, the above-mentioned raw materials and water are added to the liquid koji to conduct mashing. Lactic acid may be used if necessary.

After the mashing, the mixture is steamed and boiled at low temperature and fermented at temperature of about 20 to 30° C., to thereby conduct secondary mashing after the primary mashing.

In the case of the 21st aspect of the present invention, although no enzyme preparation is used and only the liquid koji is used, mash obtained after completion of the fermentation has high alcohol content of 18 to 20%.

The mash obtained after completion of the fermentation can be distilled with a distillator such as a microdistillation apparatus, preferably a continuous distillator, to thereby remove impurities and concentrate the mash. As a result, industrial alcohol (ethanol) with high quality, having an alcohol concentration of 95% or more can be produced.

According to the 21st aspect of the present invention, the obtained mash already has high alcohol content of 18 to 20% after completion of the fermentation, resulting in effects such as scale reduction and energy saving.

Hereinafter, the present invention will be described in detail by way of examples. However, the present invention is not limited to these examples.

EXAMPLES

Example 1

Production of Koji Mold Culture Product (Liquid Koji) Having Enhanced Activity of Plant Fiber Degradation Enzymes (I) Production of Koji Mold Culture Product (Liquid Koji)

1) Method of pre-culture: 8 g of 65%-polished barley (Stirling, made in Australia) and 100 ml of water were put into a 500-ml baffled conical flask, and the whole was sterilized at 121° C. for 15 minutes with autoclave, to thereby obtain a pre-culture medium. A white koji mold (*Aspergillus kawachii* NBRC4308) was inoculated at $1 \times 10^6$/ml into the pre-culture medium and cultured by shaking at 37° C. and 100 rpm for 24 hours, to thereby obtain a pre-culture liquid.

2) Method of main culture: Seven liquid media were prepared by adding crude barley (95% polished barley (Stirling, made in Australia)) at combination ratio of 2.0, 1.9, 1.8, 1.7, 1.6, 1.5 and 1.4% (w/vol) as shown in Table 1 to water containing 0.2% (w/vol) of potassium nitrate and 0.3% (w/vol) of potassium dihydrogen phosphate.

3,000 ml of each of the liquid media was put in a 5,000-ml jar fermentor (manufactured by B. E. Marubishi Co., Ltd.), and the whole was sterilized at 121° C. for 15 minutes with autoclave, to thereby obtain a main culture medium. Each main culture medium was inoculated with 30 ml of the above-mentioned pre-culture liquid.

After that, culture was conducted for 42 hours at a temperature of 37° C. and a stirring rate of 300 rpm and with an aeration volume of 0.5 vvm, to thereby obtain koji mold culture products (liquid koji).

(II) Measurement of Enzymatic Activities

The koji mold culture products (liquid koji) obtained in section (I) were each measured for yield of glucoamylase (GA), acid-stable α-amylase (ASAA), cellulase (CEL), and xylanase (XYL). Table 1 shows the yield of glucoamylase (GA), acid-stable α-amylase (ASAA), cellulose (CEL), and xylanase (XYL) in each of the koji mold culture products (liquid koji) obtained by culturing koji molds in the liquid media containing crude barley in different amounts.

The glucoamylase (GA) activity was measured by using a saccharification power fractional quantification kit (manufactured by Kikkoman Corporation). For measuring the acid-stable α-amylase (ASAA) activity, the method described in Sudo S. et al: J. Ferment. Bioeng., 76, 105-110 (1993), Sudo S. et al: J. Ferment. Bioeng., 77, 483-489 (1994), and Shigetoshi Sudo et al: Journal of the Brewing Society of Japan, 89, 768-774 (1994) were slightly modified. That is, acid-unstable α-amylase was inactivated by treating the culture product with acid, and then acid-stable α-amylase activity was measured with an α-amylase measurement kit (manufactured by Kikkoman Corporation) To be more specific, 9 ml of 100 mM acetic acid buffer solution (pH 3) was added to 1 ml of the culture liquid, acid treatment was conducted at 37° C. for 1 hour, and then measured with the α-amylase measurement kit (manufactured by Kikkoman Corporation).

Activities of cellulase and xylanase that are plant fiber degradation enzymes were then measured.

First, the cellulase (CEL) activity was measured by the method that reduced saccharide generated from enzymatic hydrolysis of carboxymethylcellulose (hereinafter, abbreviated as CMC) as a substrate was allowed to react with DNS (3,5-dinitrosalicylic acid), and that increase of absorbance at 540 nm was quantitated. To be more specific, 1 ml of the culture liquid was added to 1 ml of 1% CMC substrate solution (Low Viscosity™ produced by Sigma-Aldrich was dissolved in 100 mM acetic acid buffer solution (pH 5)), and the whole was subjected to enzymatic reaction at 40° C. precisely for 10 minutes. After that, 4 ml of the DNS reagent containing 0.75% of dinitrosalicylic acid, 1.2% of sodium hydroxide, 22.5% of potassium sodium tartrate tetrahydrate and 0.3% of lactose monohydrate, was added to the mixture, and the whole was well mixed, to thereby terminate the reaction. In order to quantitate the amount of reduced saccharide in the solution after the completion of the reaction, the solution after the completion of the reaction was heated in boiling water bath precisely for 15 minutes. Subsequently, the solution was cooled to room temperature, absorbance at 540 nm was determined, to thereby quantitate amount of the reduced saccharide corresponding to that of glucose. One unit of the cellulase (CEL) activity was represented by the amount of enzyme required for producing reduced saccharide corresponding to 1 μmol of glucose per minute. To be specific, the one unit of the cellulase activity was represented by the amount of enzyme required for producing reduced saccharide corresponding to 1 μmol of glucose per minute under the reaction condition of 40° C. for 10 minutes.

Next, the xylanase (XYL) activity was measured by that reduced saccharide generated from enzymatic hydrolysis of xylan derived from oat spelts as a substrate was allowed to react with DNS, and that increase of absorbance at 540 nm was quantitated. To be more specific, 0.1 ml of the culture liquid was added to 1.9 ml of 1% xylan substrate solution (Xylan, from oat spelts produced by Sigma-Aldrich was dissolved in 200 mM acetic acid buffer solution (pH 4.5)), and the whole was subjected to enzymatic reaction at 40° C. precisely for 10 minutes. After that, 4 ml of the DNS reagent containing 0.75% of dinitrosalicylic acid, 1.2% of sodium hydroxide, 22.5% of potassium sodium tartrate tetrahydrate and 0.3% of lactose monohydrate, was added to the mixture, and the whole was well mixed, to thereby terminate the reaction. In order to quantitate the amount of reduced saccharide in the solution after the completion of the reaction, the solution after the completion of the reaction was heated in boiling water bath precisely for 15 minutes. Subsequently, the solution was cooled to room temperature, absorbance at 540 nm was determined, to thereby quantitate amount of the reduced saccharide corresponding to that of xylose. One unit of the xylanase activity was represented by the amount of enzyme required for producing reduced saccharide corresponding to 1 μmol of xylose per minute under the reaction condition of 40° C. for 10 minutes.

As shown in Table 1, it was confirmed that generation balance of various enzymes differs depending on the amount of crude barley to be used. In particular, it was found that activities of cellulase (CEL) and xylanase (XYL) were apt to significantly increase in the experimental plots containing 1.8% or less crude barley to be used. In particular, cellulase (CEL) and xylanase (XYL) were generated in a balanced manner while glucoamylase (GA) and acid-stable α-amylase (ASAA) were also highly generated in a balanced manner in the 1.7% experimental plot.

Accordingly, it was revealed that activities of the enzymes other than glucoamylase (GA) and acid-stable α-amylase (ASAA), particularly the plant fiber degradation enzymes such as cellulase (CEL) and xylanase (XYL) were able to be enhanced by finely controlling the amount of barley to be used.

TABLE 1

| Amount of crude barley to be used | Enzymatic activity (U/ml) | | | |
|---|---|---|---|---|
| | GA | ASAA | CEL | XYL |
| 2.0% | 212.3 | 12.3 | 0.07 | 3.3 |
| 1.9% | 223.5 | 11.4 | 0.08 | 3.6 |
| 1.8% | 224.5 | 10.6 | 0.15 | 6.4 |
| 1.7% | 213.3 | 10.2 | 0.20 | 8.9 |
| 1.6% | 204.6 | 9.5 | 0.17 | 8.7 |
| 1.5% | 194.5 | 8.5 | 0.16 | 8.0 |
| 1.4% | 187.4 | 7.4 | 0.14 | 7.0 |

Example 2

Alcohol Fermentation Using Koji Mold Culture Product (Liquid Koji) Having Enhanced Activity of Plant Fiber Degradation Enzymes Alcohol fermentation was carried out using the koji mold culture products (liquid koji) obtained in Example 1 by culturing with the liquid media to which crude barley was added in an amount of 2.0% (w/vol), 1.7% (w/vol) and 1.4% (w/vol).

Koji mold culture products were each obtained as in Example 1 by culturing koji molds with the liquid media each prepared by adding thereto crude barley in an amount of 2.0% (w/vol) for control plot, 1.7% (w/vol) for plot 1 of the present invention, and 1.4% (w/vol) for plot 2 of the present invention. 70 ml of each of the koji mold culture products was used for barley mashing by 184.6 g in total in the mashing combination shown in Table 2. The temperature for fermentation was kept at 25° C. in three-step mashing which comprises 5 days of primary mashing, 2 days of secondary mashing and 13 days of tertiary mashing.

As additional barley, 65%-polished Stirling made in Australia was used that had been washed with water, followed by 60-minute immersion, 30-minute drainage and then 35-minute steaming. In addition, 42.4 g of additional barley was fed in the primary mashing. Shochu yeast (Kagoshima yeast) was used as the yeast, and it was inoculated 50 µl of the shochu yeast that had been statically cultured in the YPD medium at 30° C. for 48 hours.

TABLE 2

|  | Mash | | | |
|---|---|---|---|---|
|  | Primary | Secondary | Tertiary | Total |
| Additional barley (g) | 42.4 | 71.1 | 71.1 | 184.6 |
| Water (ml) | 45.0 | 107.2 | 38.2 | 190.4 |
| Koji mold culture product (liquid koji) (ml) | 70.0 | — | — | 70.0 |
| 90% lactic acid (ml) | 0.2 | — | — | 0.2 |

FIG. 1 shows the process of fermentation. The process of fermentation proceeded without problems in every experimental plots. In particular, the fermentation proceeded aggressively in the 1.7% plot in which various enzymes were generated in a balanced manner. The resultant final mashes had alcohol contents of 18.0% for the 2.0% plot (control plot), 19.2% for the 1.7% plot (plot 1 of the present invention) and 18.6% for the 1.4% plot (plot 2 of the present invention). That is, high alcohol content was observed in the 1.7% plot (plot 1 of the present invention).

Figure 2:
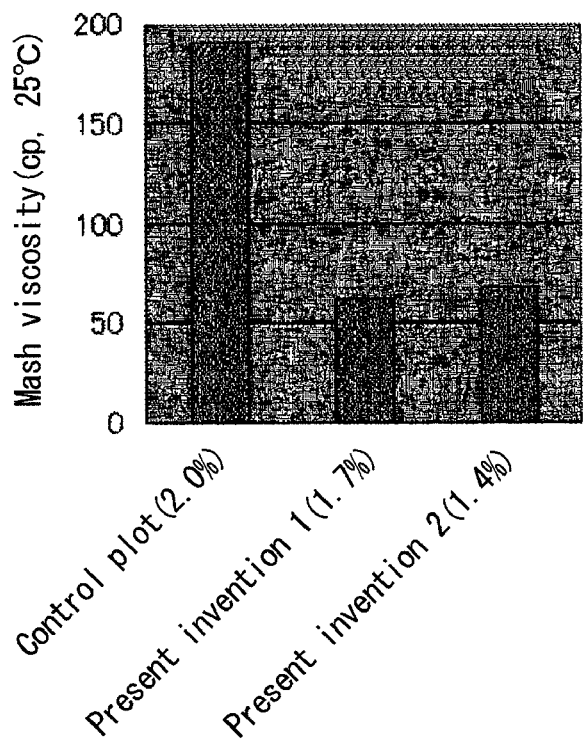
FIG. 2 is a graph showing measurement results of mash viscosities of barley shochu mashes obtained by using various liquid koji having different amounts of crude barley to be used in Example 2.

In addition, FIG. 2 shows results of viscosity measurement of final mashes with a rotational viscometer. As evident from FIG. 2, viscosities in the 1.7% plot (plot 1 of the present invention) and 1.4% plot (plot 2 of the present invention), each of which has an enhanced activity of any one of cellulase (CEL) and xylanase (XYL), significantly decreased as compared to that in the 2.0% plot (control plot). The decrease was supposed to occur owing to decomposition of the plant fiber included in large amount in barley as raw material by action of cellulase (CEL) or xylanase (XYL). The decrease in viscosity of mash is supposed to give great effects such as improvement in flowability of mash, facilitation of liquid transfer and promotion of efficiency in distillation operations.

From the results, it was revealed that plant fiber degradation enzyme such as cellulase (CEL) and xylanase (XYL) were able to be simultaneously generated and accumulated together with at least glucoamylase and acid-stable α-amylase in koji mold culture product by controlling amount of raw material to be used upon culturing koji molds in a liquid medium, the liquid medium containing as the culture raw material the cereal or the like of which surface is entirely or partly covered with at least husks. It was confirmed that when alcohol fermentation was carried out by using the koji mold culture product (liquid koji) in which activities of those plant fiber degradation enzymes were enhanced, not only amount of alcohol to be obtained was increased, but also viscosity of mash was decreased. Thus, it was provided possibility in significant promotion of efficiency in the production.

The mash can produce barley shochu with subsequent single distillation, and easily provides industrial alcohol (ethanol) with continuous distillation.

Example 3

Production of Dry Product of Koji Mold Culture Product (I) Production of Koji Mold Culture Product (Liquid Koji)
1) Method of pre-culture: 8 g of 65%-polished barley (Stirling, made in Australia) and 100 ml of water were put into a 500-ml baffled conical flask, and the whole was sterilized at 121° C. for 15 minutes with autoclave, to thereby obtain a pre-culture medium. A white koji mold (*Aspergillus kawachii* NBRC4308) was inoculated at $1\times10^6$/ml into the pre-culture medium and cultured by shaking at 37° C. and 100 rpm for 24 hours, to thereby obtain a pre-culture liquid.

2) Method of main culture: A liquid medium containing 2.0% (w/vol) of 98%-polished barley (Stirling, made in Australia), 0.2% (w/vol) of potassium nitrate and 0.3% (w/vol) of potassium dihydrogen phosphate was prepared. 3,000 ml of the liquid medium was put into a 5,000-ml jar fermentor (manufactured by B. E. Marubishi Co., Ltd.), and the whole was sterilized at 121° C. for 15 minutes with autoclave, to thereby obtain a main culture medium. The main culture medium was inoculated with 30 ml of the above-mentioned pre-culture liquid. After that, culture was conducted for 42 hours at a temperature of 37° C., a stirring rate of 300 rpm and an aeration volume of 0.5 vvm, to thereby obtain koji mold culture product (liquid koji).

(II) Production of Dry Product of Koji Mold Culture Product (Liquid Koji)

200 ml of the koji mold culture product (liquid koji) obtained in section (I) was pre-frozen at −30° C. for 2 hours. After that, the resultant was dried at 25° C. at a vacuum degree of 0.5 Torr for 24 hours, to thereby obtain 2.7 g of dry product of the koji mold culture product (liquid koji), that is, vacuum freeze dry product of the koji mold culture product.

(III) Measurement of Enzymatic Activities

For the undried koji mold culture product (liquid koji), that is, undried product, which was obtained in section (I) and the dried product of koji mold culture product (liquid koji), that is, dry product, which was obtained in section (II), yields of glucoamylase (GA) and acid-stable α-amylase (ASAA) were measured.

The glucoamylase activity was measured by using a saccharification power fractional quantification kit (manufactured by Kikkoman Corporation). For measuring the acid-stable α-amylase activity, the method described in Sudo S. et al: J. Ferment. Bioeng., 76, 105-110 (1993), Sudo S. et al: J. Ferment. Bioeng., 77, 483-489 (1994), and Shigetoshi Sudo et al: Journal of the Brewing Society of Japan, 89, 768-774 (1994) was slightly modified. That is, acid-unstable α-amylase was inactivated by treating the culture product with acid, and then acid-stable α-amylase activity was measured with an α-amylase measurement kit (manufactured by Kikkoman Corporation). To be more specific, 9 ml of 100 mM acetic acid buffer solution (pH 3) was added to 1 ml of culture liquid, and acid treatment was conducted at 37° C. for 1 hour, and measured with the α-amylase measurement kit (manufactured by Kikkoman Corporation).

The enzymatic activities of the dry product of koji mold culture product (liquid koji), that is, dry product, were measured with the stuff obtained by dissolving 270 mg of the dry product of koji mold culture product (liquid koji), that is, dry product, in 20 ml of 10 mM acetate buffer (pH 5).

Table 3 shows the measurement results of the enzymatic activities in the undried product obtained in section (I) and the dry product obtained in section (II).

As shown in Table 3, it was confirmed that the liquid koji did not lose its enzymatic activities even when the liquid koji was freeze-dried, and the dry product of liquid koji thus was able to be used sufficiently for shochu mashing.

TABLE 3

| | Enzymatic activity (U/ml) | |
|---|---|---|
| | Glucoamylase | Acid-stable α-amylase |
| Undried product | 156.8 | 10.8 |
| Dry product | 154.0 | 10.2 |

Example 4

Alcohol Fermentation Using Koji Mold Culture Product (Liquid Koji)

Alcohol fermentation was conducted using the undried product and the dry product each obtained in Example 3 (representing undried plot and dry plot, respectively).

That is, 100 ml of the undried product or 1.35 g of the dry product each obtained in Example 3 was used for barley mashing by 3.7 g in total in the mashing combination as shown in Tables 4 and 5, respectively. The temperature for fermentation was kept at 25° C. and two-step mashing was conducted which comprises 4 days of primary mashing and 17 days of secondary mashing.

As additional barley, 65%-polished Stirling made in Australia was used that had been washed with water, followed by 60-minute immersion, 30-minute drainage, and then 35-minute steaming. Shochu yeast (Kagoshima yeast) was used as the yeast, and it was inoculated 50 μl of the shochu yeast that had been statically cultured in the YPD medium at 30° C. for 48 hours.

TABLE 4

| | Undried plot (mashing with undried product) | | |
|---|---|---|---|
| | Primary mashing | Secondary mashing | Total |
| Additional barley (g) | 100 | 207 | 307 |
| Water (ml) | 50 | 279 | 329 |
| Undried product (ml) | 100 | — | 100 |
| Lactic acid for brewing (ml) | 0.2 | — | 0.2 |

TABLE 5

| | Dry plot (mashing with dry product) | | |
|---|---|---|---|
| | Primary mashing | Secondary mashing | Total |
| Additional barley (g) | 100 | 207 | 307 |
| Water (ml) | 150 | 279 | 429 |
| Dry product (ml) | 1.35 | — | 1.35 |
| Lactic acid for brewing (ml) | 0.2 | — | 0.2 |

Figure 3:
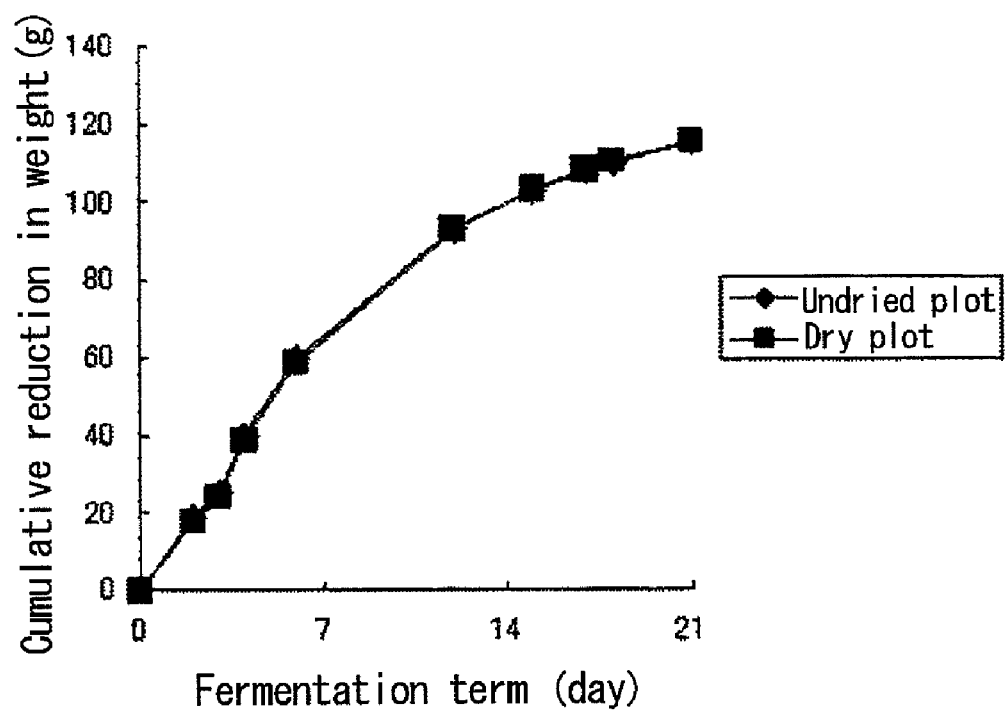
FIG. 3 is a graph showing the processes of fermentation in the undried plot and the dry plot in Example 4, depending on cumulative reduction in weight.

FIG. 3 shows processes of fermentation of mashes in the undried plot and the dry plot, which were obtained by cumulative reduction in weight of the mashes.

As a result, as evident from FIG. 3, almost no difference regarding the process of fermentation was observed between the undried plot that represents undried product mashing and the dry plot that represents dry product mashing.

Alcohol contents in the obtained final mashes were 19.6% for the undried plot and 19.4% for the dry plot. Thus, fermentation proceeded well in the both experimental plots.

Example 5

Production of Ethanol Using Crude Rice Koji Mold Culture Product (Liquid Koji)

(I) Production of Crude Rice Koji Mold Culture Product (Liquid Koji)

1) Method of pre-culture: 8 g of 90%-polished rice (Koshihikari) and 100 ml of water were put into a 500-ml baffled conical flask, and the whole was sterilized at 121° C. for 15 minutes with autoclave, to thereby obtain a pre-culture medium. A white koji mold (*Aspergillus kawachii* NBRC4308) was inoculated at 1×10$^6$/ml into the pre-culture medium and cultured by shaking at 37° C. and 100 rpm for 24 hours, to thereby obtain a pre-culture liquid.

2) Method of main culture: 8 g of crude rice (Koshihikari) which was removed only chaffs thereof, 0.2 g of $KNO_3$, 0.3 g of $KH_2PO_4$, and 100 ml of water were put into a 500-ml baffled conical flask, and the whole was sterilized at 121° C. for 15 minutes with autoclave, to thereby obtain a main culture medium (5 flasks of the main culture medium were prepared). 1-ml each of the pre-culture liquid was inoculated to the main culture medium and then cultured with shaking at 37° C. and 100 rpm for 72 hours, to thereby obtain a crude rice koji mold culture product (liquid koji).

Table 6 shows enzymatic activities in the resultant crude rice koji mold culture product (liquid koji).

As shown in Table 6, the resultant crude rice koji mold culture product (liquid koji) was confirmed to have good glucoamylase and acid-stable α-amylase activities.

TABLE 6

| Enzymatic activity | Crude rice koji mold culture product |
|---|---|
| Glucoamylase activity | 135 U/ml |
| Acid-stable α-amylase activity | 11 U/ml |

(II) Feeding and Fermentation

Feeding combination was as shown in Table 7. Shochu yeast (Kagoshima yeast) was cultured in 10 ml of the YPD medium at 30° C. for 1 day. After that, 1 ml of culture liquid of the yeast was centrifuged, and the precipitated yeast was washed twice with sterilized water. A total amount of the collected yeast was used as the yeast.

The crude rice koji mold culture product (liquid koji) obtained in section (I), the above-mentioned yeast, additional rice (polished rice of Koshihikari), 90% lactic acid and water were put into a continuous steaming and boiling apparatus. Fermentation was conducted under the condition of constant temperature of 25° C. for 16 days. After 3 days from the primary mashing, secondary mashing was conducted.

TABLE 7

| | Amount of use | | |
|---|---|---|---|
| Raw material | Primary mashing | Secondary mashing | Total |
| Crude rice koji mold culture product (liquid koji) (ml) | 350 | — | 350 |
| Additional rice (g) | 300 | 600 | 900 |
| Water (ml) | 500 | 650 | 1150 |
| 90% lactic acid (ml) | 1 | — | 1 |

A mash of the crude rice koji mold culture product (liquid koji) after completion of the fermentation, which was obtained as described above, had an alcohol content of 19.1%.

(III) Production of Industrial Alcohol (Ethanol)

The mash of the crude rice koji mold culture product (liquid koji) after completion of the fermentation, which was obtained in section (II), was continuously distilled with a microdistillation apparatus (HP-1000T special type, manufactured by Sibata Scientific Technology Ltd.), to thereby collect industrial alcohol (ethanol).

The obtained industrial alcohol (ethanol) had an alcohol content of 95.3%.

Further, a mash having high alcohol content was also able to be produced when it was employed a koji mold culture product (liquid koji) with crude barley as raw material. Consequently, industrial alcohol (ethanol) with no quality defect was able to be produced.

As described above, according to the present invention, it was revealed that industrial alcohol (ethanol) was able to be produced by using koji mold culture product (liquid koji).

INDUSTRIAL APPLICABILITY

According to the first aspect of the present invention, liquid koji having enhanced activity of plant fiber degradation enzymes such as cellulolytic enzymes (cellulose) and xylanolytic enzymes can be produced by liquid culturing instead of solid culturing without using an expensive plant fiber degradation enzyme preparation and a recombinant bacterium.

In addition, according to the sixth aspect of the present invention, there can be produced liquid koji dry product which has high activities of glucoamylase, acid-stable α-amylase, and plant fiber degradation enzymes and is further excellent in handling property. Further, the product is in dry state, so there is a merit that it is timely available even for unexpected production.

According to the 21st aspect of the present invention, industrial alcohol (ethanol) can efficiently be produced by a fermentation method using the liquid koji sufficiently having enzymatic activities required for alcohol fermentation.

Thus, the present invention is expected to be effectively utilized in a field of production of foods and drinks, a field of chemical industry and a field of energy industry.

The invention claimed is:

1. A method of producing liquid koji having enhanced activity of a cellulolytic enzyme and a xylanolytic enzyme comprising:
    culturing white koji molds, black koji molds, or a combination thereof with a liquid medium containing at least one cereal selected from the group consisting of barley, naked barley and wheat, the cereal having a surface which is entirely covered with husks, wherein an amount of the cereal in the liquid medium is from 1.4 to 1.8% (w/vol),
    generating and accumulating simultaneously, a glucoamylase, an acid-stable α-amylase, a cellulase and a xylanase, in the liquid koji.

2. The method of producing liquid koji according to claim 1, wherein the culturing step is carried out at 37° C. for 42 hours.

3. A method of producing a liquid koji dry product comprising freeze-drying the liquid koji obtained by the method of claim 1 to obtain the liquid koji dry product.

4. A method of producing an enzyme preparation comprising, purifying the liquid koji of claim 1 or 2 to obtain a purified koji, and combining the koji with at least one pharmaceutically acceptable excipient.

5. A method of producing at least two enzymes selected from the group consisting of a glucoamylase, an acid-stable α-amylase, a cellulase and a xylanase comprising
    culturing white koji molds, black koji molds, or a combination thereof with a liquid medium containing at least one cereal selected from the group consisting of barley, naked barley and wheat, the cereal having a surface which is entirely covered with husks, wherein an amount of the cereal in the liquid medium is from 1.4 to 1.8% (w/vol),
    generating and accumulating simultaneously, at least two enzymes selected from the group consisting of glucoamylase, acid-stable α-amylase, a cellulase and a xylanase, in the liquid koji.

6. The method of claim 5, wherein the culturing step is carried out at 37° C. for 42 hours.

* * * * *